United States Patent [19]

Boeck

[11] Patent Number: 4,683,204
[45] Date of Patent: Jul. 28, 1987

[54] PROCESS FOR PRODUCING ANTIBIOTIC A80190

[75] Inventor: LaVerne D. Boeck, Indianapolis, Ind.

[73] Assignee: Eli Lilly and Company, Indianapolis, Ind.

[21] Appl. No.: 658,977

[22] Filed: Oct. 9, 1984

[51] Int. Cl.$^4$ .................. C12P 13/00; C12N 1/20; C12R 1/03

[52] U.S. Cl. .................. 435/128; 435/253; 435/825

[58] Field of Search .................. 435/128, 253, 825

[56] References Cited

U.S. PATENT DOCUMENTS

| | | | |
|---|---|---|---|
| 4,148,882 | 4/1979 | Celmer et al. | 424/122 |
| 4,195,079 | 3/1980 | Celmer et al. | 424/122 |
| 4,293,650 | 12/1981 | Florent et al. | 435/119 |
| 4,407,946 | 10/1983 | Labeda et al. | 435/75 |

OTHER PUBLICATIONS

J. Tone et al., "CP-47, 433 and CP-47, 434, New Polycyclic Ether Antibiotics Produced by a New Species of Actinomadura, in "Current Chemotherapy and Infectious Disease", J. D. Nelson and C. Grassi, Eds., vol. I, American Society for Microbiology, Washington, D.C. 1980, pp. 469–470.

Nakamura et al., "A New species of Actinomadura Producing a Polyether Antibiotic, Cationomycin", J. Antibiotics 36, 1468–1472 (1983).

Derwent Abstract No. 83-834403/49 of European Patent 95-154-A to Fujisawa Pharm. KK.

"Polyether Antibiotics, Naturally Occurring Acid Ionophores, vol. 1, Biology", J. W. Westley, Ed., Marcel Dekker Inc., New York, 1982, pp. viii–xi.

"Polyether Antibiotics: Naturally Occurring Acid Ionophores, vol. 2, Chemistry, J. W. Westley Ed., Marcel Dekker, Inc., New York, 1983, p. 197 and excerpts from pp. 223–224.

Primary Examiner—Thomas G. Wiseman
Assistant Examiner—Elizabeth C. Weimar
Attorney, Agent, or Firm—Nancy J. Harrison; Leroy Whitaker

[57] ABSTRACT

Improved fermentation process for producing the polyether antibiotic A80190 which comprises cultivating a new strain of *Actinomadura Oligospora*, NRRL 15878, and the biologically purified culture of this microorganism are provided.

5 Claims, No Drawings

PROCESS FOR PRODUCING ANTIBIOTIC A80190

SUMMARY OF THE INVENTION

This invention relates to a new microorganism, Actinomadura oligospora NRRL 15878, which produces the polyether antibiotic A80190. This invention also relates to a process for producing A80190 by culturing the novel strain of *Actinomadura oligospora* NRRL 15878 under submerged aerobic fermentation conditions until a substantial level of the antibiotic is produced. A80190 is extracted from the fermentation broth and from the mycelium with polar organic solvents and is separated and further purified by techniques such as column chromatography.

A80190 is an antibacterial and anticoccidial agent. It also improves feed-utilization efficiency in ruminants and acts as a growth promotant in monogastric animals.

DETAILED DESCRIPTION OF THE INVENTION

Improved methods for producing antibiotics are of great importance. Commonly, the culture isolated from the natural state (the "wild type") produces the antibiotic in low yield. Often, antibiotic production is erratic. Strains with enhanced potency and strains which consistently produce the antibiotic are, therefore, of great value.

This invention provides an improved process for preparing antibiotic A80190 by culturing an A80190-producing strain of *Actinomadura oligospora* NRRL 15878 under submerged aerobic conditions in a suitable culture medium until substantial antibiotic activity is produced. The antibiotic is recovered using various isolation and purification procedures understood in the art.

A80190, a new member of the group of polyether antibiotics, is the subject of the co-pending application of Robert L. Hamill and Raymond C. Yao entitled "ANTIBIOTIC A80190", attorney docket No. X-6594, Ser. No. 658,976, filed Oct. 9, 1984, now U.S. Pat. No. 4,582,822, issued April 15, 1986. Westley (John W. Westley, "Polyether Antibiotics: Naturally Occurring Acid Ionophores, Vol 2, Chemistry," Marcel Dekker: New York, 1983) has separated existing polyethers by class and type. Using Westley's system, A80190 is a new member of the Class 1b, type (1), group of polyethers because it has one spiroketal system. Other members of this group include A-28695 A and B (U.S. Pat. No. 3,839,558); A204I and II (U.S. Pat. No. 3,705,238); A-32887 (U.S. Pat. No. 4,133,876); carriomycin; etheromycin; CP-47,434, RP37454 and the X-14868 antibiotics.

CHARACTERISTICS OF A80190

Antibiotic A80190 has been assigned structure 1, based on X-ray crystallographic studies:

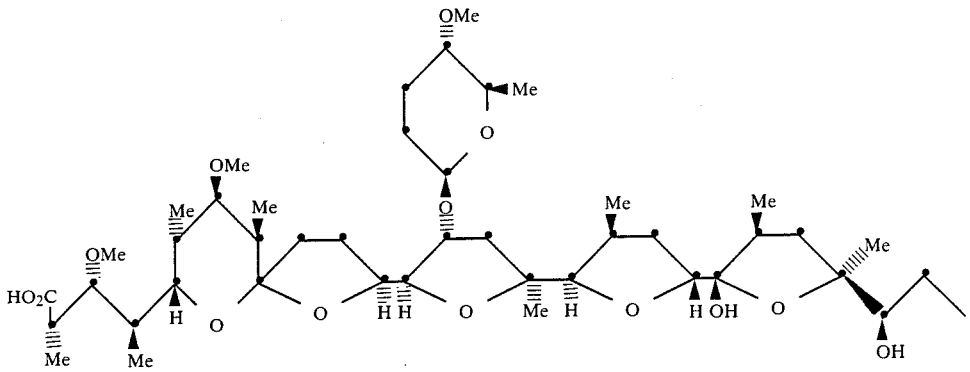

A80190 (in its free acid form) has the following characteristics:

State: white crystals (from acetone-water)
Mp: 98°–100° C. or 120°–122° C. (more frequently); probably varies with the degree of solvation
pKa: 6.2(66% aqueous dimethylformamide) $[\alpha]^{25}D$: −26° (c 1, CHCl$_3$)
Molecular weight: 828 (field desorption mass spectrometry)
Empirical formula: $C_{44}H_{76}O_{14}$
UV: no absorbance
IR: (CHCl$_3$) shows absorption maxima at the following frequencies (cm$^{-1}$): 3019, 2970, 2936, 2827, 1721, 1457, 1402, 1376, 1314, 1163, 1105, 1092, 1083, 1056, 1022, 1006, 989, 980, 945, 934, 917, 892 and 859

Elemental Analysis:

|  | Found | Calcd |
|---|---|---|
| Carbon | 63.35 | 63.77 |
| Hydrogen | 9.17 | 9.18 |
| Oxygen | 27.10 | 27.05 |

Solubility: Insoluble in water; soluble in lower alcohols such as methanol, ketones such as acetone, esters such as ethyl acetate, halogenated hydrocarbons such as chloroform and hydrocarbons such as diethyl ether, benzene, toluene and warm hexane.

The microorganism of this invention, which is useful for the preparation of antibiotic A80190, is a variant strain which was obtained from a culture isolated from a soil sample from India. Cultures of the A80190-producing organisms, i.e. the parent soil isolate and the variant strain, have been deposited and made part of the stock culture collection of the Northern Regional Research Center, Agricultural Research, North Central Region, 1815 North University Street, Peoria, Ill., 61604, from which they are available to the public under the accession numbers NRRL 15877 (parent) and NRRL 15878 (variant of this invention).

Taxonomic studies of the variant strain were carried out by Frederick P. Mertz of the Lilly Research Laboratories. Based on these studies, the variant and the parent cultures are classified as members of a new species of the genus Actinomadura for which the name *Actinomadura oligospora* sp. nov. is proposed. This classification is based on direct laboratory comparisons with similar species and examination of published descriptions [M. Goodfellow and G. Alderson, "Numerical Taxonomy of Actinomadura and Related Actinomycetes," *J. Gen. Microbiol.* 112:95-111 (1970); M. Goodfellow and K. P. Schaal, "Identification Methods for Nocardia, Actinomadura and Rhodococcus," p. 261-276 In F. A. Skinner and D. W. Lovelock (ed.), "Identification Methods for Microbiologists," 2nd ed., The Society for Applied Microbiology Technical Series No. 14, Academic Press, New York, 1979; L. H. Huang, "*Actinomadura macra* sp. nov., the Producer of Antibiotics CP-47,433 and CP-47,434," *Int. J. Syst. Bacteriol.* 30:565-568 (1980); and H. A. Lechevalier and M. P. Lechevalier, "A Critical Evaluation of the Genera of Aerobic Actinomycetes," p. 393-405, In H. Prauser (ed.), The Actinomycetales. Gustav Fischer Verlog, Jena].

METHODS USED

The methods recommended by the International Streptomyces Project (ISP) for the characterization of Streptomyces species [E. B. Shirling and D. Gottlieb, "Methods for Characterization of Streptomyces Species," *Internat. J. Syst. Bacteriol.* 16:313-340 (1966)] have been followed along with certain supplementary tests [D. J. Blazevic and G. M. Ederer, "Principles of Biochemical Tests in Diagnostic Microbiology," John Wiley and Sons, Inc., New York, 1975].

Carbon utilization was determined with ISP No. 9 basal medium to which filter-sterilized carbon sources were added to equal a final concentration of 1.0 percent. Plates were incubated at 30° C. and read after 14 days.

Melanoid pigment production (chromogenicity) was determined with ISP No. 1 (tryptone-yeast extract broth), ISP No. 6 (peptone-yeast extract iron agar), ISP No. 7 (tyrosine agar) and modified ISP No. 7 which has tyrosine removed.

Starch hydrolysis was determined by testing for the presence of starch with iodine on ISP No. 4 (inorganic salts-starch agar) plates (See Blazevic and Ederer, supra).

Morphology was studied using an optical light microscope. A scanning electron microscope (SEM) was used to study the spore surface ornamentation.

NaCl tolerance was measured by adding NaCl to ISP No. 2 agar to equal the concentration desired.

ICSS-NBS Centroid Color Charts, standard sample No. 2106 (National Bureau of Standards, 1958, U.S. Department of Commerce, Washington, D.C.) and the Color Harmony Manual (4th ed., Container Corporation of America, Chicago, Ill., 1958) were used to assign color names.

The isomers of diaminopimelic acid (DAP) and the carbohydrates in hydrolysates of whole cells were established by the chromatographic methods of Becker et al. [B. Becker, M. P. Lechevalier, R. E. Gordon, and H. A. Lechevalier, "Rapid Differentiation between Nocardia and Streptomyces by Paper Chromatography of Whole-cell Hydrolysates," *Appl. Microbiol.* 12:421-423 (1964)]and of Lechevalier [M. P. Lechevalier, "Identification of Aerobic Actinomycetes of Clinical Importance," *J. Lab. Clin. Med.* 71:934-944 (1968)].

Resistance to lysozyme was measured by methods recommended by Gordon [R. E. Gordon and D. A. Barnett, "Resistance to Rifampin and Lysozyme of Strains of Some Species of Mycobacterium and Nocardia as a Taxonomic Tool," *Int. J. Syst. Bacteriol.* 27, 176-178 (1977)].

Resistance to antibiotics was measured by padding antibiotic sensitivity discs onto the surface of seeded ISP No. 2 agar plates.

Phosphatase and urease were determined by methods described by Blazevic, supra.

Mycolic acids were determined by a method based on techniques described by Minnikin [D. E. Minnikin, L. Alshamaony and M. Goodfellow, "Differentiation of Mycobacterium, Nocardia, and Related Taxa by Thin-Layer Chromatographic Analysis of Whole-organism Methanolysates," *J. Gen. Microbiol.* 88:200-204 (1975)]

Phospholipid analysis was performed as described by Lechevalier [M. P. Lechevalier, C. De Bievre and H. Lechevalier, "Chemotaxonomy of Aerobic Actinomycetes: Phospholipid Composition," *Biochemical Systematics and Ecology* 5, 249-260 (1977)].

CULTURAL CHARACTERISTICS

Growth of the organism was generally poor on chemically defined media but better on complex organic media. Aerial mycelia were absent except for trace amounts on ISP No. 4 and sodium butyrate agar. When spores were present, their color was oyster white in the Tresner and Backus System [H. D. Tresner and E. J. Backus, "System of Color Wheels for Streptomycete Taxonomy," *Appl. Microbiol.* 11:335-338 (1956)]. The color of the reverse side was yellowish gray to brown. No soluble pigments were produced, except for the production of a very light brown soluble pigment in ISP No. 2 and a dark brown soluble pigment in yeast-dextrose agar. Table I presents these cultural characteristics.

TABLE I

Cultural Characteristics of NRRL 15878 and *A. macra* on Various Agar Media[a]

| Agar Media | | NRRL 15878 | A. macra |
|---|---|---|---|
| ISP No. 2 | G: | Good (moist surface) | Abundant (39.gy.r0) |
| | R: | 61.gy.Br | 43.m.rBr → 56.deep Br. |
| | Am: | None | None |
| | Sp: | Very light brown | Very light brown |
| Isp No. 3 | G: | Poor | Fair |
| | R: | 93.y Gray | 5.m.Pink |
| | Am: | Trace: b White few scattered individual clumps | None |
| | SP: | None | None |
| ISP No. 4 | G: | Poor | Fair to poor |
| | R: | 93.y Gray | 5 m. Pink |
| | Am: | Trace: b White few scattered individual clumps | None |
| | SP: | None | None |
| ISP No. 5 | G: | Poor | Good |
| | R: | 93.y Gray | 48.v.0 |
| | Am: | None | None |
| | Sp: | None | None |
| ISP No. 7 | G: | Poor (moist surface) | Fair |
| | R: | 79.1.gy.y.Br | 48.v.0 |
| | Am: | None | None |
| | Sp: | Light-brown | None |
| Czapek's | G: | Fair | Fair |
| | R: | 93.y Gray | 93.y Gray |
| | Am: | None | None |
| | Sp: | None | None |
| Emerson's | G: | Good (edges peeled back) | Good |
| | R: | 77.m.yBr | 267. Black |
| | Am: | None | Trace: 5fe l.gy.rBr |
| | Sp: | None | None |
| Glucose | G: | Good (moist surface) | Good |

TABLE I-continued
Cultural Characteristics of NRRL 15878 and A. macra on Various Agar Media[a]

| Agar Media | | NRRL 15878 | A. macra |
|---|---|---|---|
| Aspara- | R: | 90.gy.Y | 26.s.y Pink |
| gine | Am: | None | Fair: a White → 7ca 1.y Pink |
| | Sp: | None | None |
| Tomato- | G: | Abundant (moist surface) | Good |
| paste | R: | 79.l.gy.y.Br | 39.gy.r0 |
| Oatmeal | Am: | None | Trace: 2 White (edges only) |
| | Sp: | None | None |
| Yeast- | G: | Abundant (moist surface) | Abundant (moist surface) |
| dextrose | R: | 81.d.gy.y Br | 59.d.Br |
| | Am: | None | Slight trace: Gray |
| | Sp: | Dark-brown | Dark-brown |
| Sodium | G: | Good | Fair |
| Butyrate | R: | 93.y Gray | 78.d.yB |
| | Am: | Fair: b White | None |
| | Sp: | None | None |
| Calcium | G: | Fair | Fair |
| Malate | R: | 93.y Gray | 26.s.y. Pink |
| | Am: | None | None |
| | Sp: | None | None |

[a] G = growth
R = reverse
Am = aerial mycelium
Sp = soluble pigment

MORPHOLOGICAL CHARACTERISTICS

Spore chains were sparsely produced on ISP No. 4 and sodium butyrate agar. Sporophores contained approximately 10 spores per chain, and were generally flexuous as in the Rectus-flexibilis (RF) configuration. However, hooked sporophores were also observed. The aerial hyphae had a tendency to clump together. Spore shape was oblong and ranged in size from 0.5–0.7 μm by 0.9–1.3 μm. The average spore size measured 1.1 by 0.6 μm. The spore surface ornamentation was smooth.

PHYSIOLOGICAL CHARACTERISTICS

Table II lists the carbohydrate utilization pattern of the strain as compared to that of *A. macra*. ISP medium No. 9 was used as a basal medium. The addition of vitamin B$_1$ or the use of Luedemann's medium [G. M. Luedemann and B. Brodsky, "Micromonospora carbonacea sp. n., an Everinomicin-producing Organism," *Antimicrob. Agents Chemother.* 1964, 47–52] produced slightly better growth, but no change in carbon utilization. Adonitol, cellobiose, glucose, and ribose were utilized. Questionable utilization was noted with fructose and xylose. Arabinose, cellulose, dextran, galactose, i-inositol, inulin, lactose, mannitol, mannose, melizitose, melibiose, raffinose, rhamnose, salicin, sucrose, trehalose, and xylitol were not utilized for growth.

TABLE II
Carbon Utilization Pattern of NRRL 15878 and A. macra[a]

| Carbon Source | NRRL 15878 | A. macra |
|---|---|---|
| control | − | − |
| adonitol | + | − |
| L-arabinose | − | − |
| cellobiose | + | − |
| cellulose | − | ND |
| dextran | − | ND |
| D-fructose | ± | − |
| D-galactose | − | ± |
| D-glucose | + | + |
| i-inositol | − | ± |
| inulin | − | ND |
| D-lactose | − | − |
| mannitol | − | − |
| D-mannose | − | − |
| D-melezitose | − | − |
| D-melibiose | − | − |
| raffinose | − | − |
| L-rhamnose | − | − |
| ribose | + | ± |
| salicin | − | − |
| sucrose | − | + |
| trehalose | − | + |
| xylitol | − | ND |
| D-xylose | ± | ± |

[a] + = utilized, − = not utilized, ± doubtful if utilized, ND = not done

Table III lists the resistance of the strain to various antibiotics at the concentrations indicated and compares it to that of *A. macra*.

TABLE III
Resistance to Antibiotics by NRRL 15878 and A. macra[a]

| Antibiotic | Concentration | | NRRL 15878 | A. macra |
|---|---|---|---|---|
| Bacitracin | 10 | units | + | − |
| Cephalothin | 30 | μg | + | + |
| Gentamicin | 10 | μg | − | − |
| Lincomycin | 2 | μg | + | + |
| Neomycin | 30 | μg | − | − |
| Oleandomycin | 15 | μg | − | |
| Pencillin G | 10 | units | + | + |
| Rifampin | 5 | μg | + | + |
| Streptomycin | 10 | μg | − | + |
| Tetracycline | 30 | μg | − | − |
| Tobramycin | 10 | μg | − | − |
| Vancomycin | 30 | μg | − | − |

[a] + = resistant (no zones of inhibition)
− = sensitive (zones of inhibition)

Strain NRRL 15878 grew at temperatures from 15°–42° C., and tolerated up to 2 percent NaCl. It produced catalase, phosphatase and urease.

Strain NRRL 15878 degraded casein, DNA, esculin, and gelatin, but not adenine, calcium malate, chitin, elastin, guanine, hippurate, hypoxanthine, keratin, starch, testosterone, tyrosine or xanthine.

CELL-WALL ANALYSIS

Hydrolyzed whole cells contained the meso isomer of diaminopimelic acid. Sugars present in whole cell hydrolysates were as follows: glucose, mannose, madurose, and ribose. The cell-wall type according to Becker, supra, is type III, and the sugar pattern is type B (Lechevalier, 1968). A qualitative analysis of whole-cell methanolysates for mycolic acids yielded questionable results. It is doubtful that the culture contains mycolic acids. A type PI phospholipid pattern was found. Type PI contains no nitrogenous phospholipids and is characteristic of the genus Actinomadura (Lechevalier, 1977).

IDENTITY OF THE STRAIN

Strain NRRL 15878 has a Type III cell wall, Type B whole-cell sugar pattern, and a Type PI phospholipid pattern. This chemotaxonomic information plus its general cultural characteristics are consistent with the assignment of the strain to the genus Actinomadura Lechevalier and Lechevalier (Lechevalier, 1970).

Comparison of its characteristics to those in published descriptions of known species of Actinomadura show that the culture is similar to *A. pelletieri* (Laveran 1906) Lechevalier and Lechevalier, 1970 and to *A. macra* (Huang, 1980).

The culture resembles *Actinomadura pelletieri* mainly by the absence, or at least the rare occurrence, of aerial mycelia. Morphology of sporophores, when produced, is similar to that described in the literature (Goodfellow, 1979). The two cultures also possess a number of physiological characteristics in common. However, the cultural and physiological differences are sufficient to separate them as distinct species.

According to Lechevalier (1970), *A. pelletieri* is represented exclusively by a group of clinical isolates. The original description of *A. pelletieri* by Gordon [R. E. Gordon, "Some Criteria for the Recognition of *Nocardia madurae* (Vincent) Blanchard," *J. Gen. Microbiol* 45:355–364 (1966)] describes it as being a bright red culture. NRRL 15878 does not produce this pigment. *A. pelletieri* degrades elastin, hypoxanthin, keratin, tyrosine, utilizes trehalose, reduces nitrate, and grows at 45° C.; but NRRL 15878 does not have these characteristics. NRRL 15878 utilizes adonitol and cellobiose, degrades esculin and DNA, and is resistant to lysozyme; but *A. pelletieri* does not have these characteristics. The new culture is, therefore, considered to be a different species than *A. pelletieri*.

Because of the culture's similarity to *A. macra*, simultaneous laboratory comparisons were made. NRRL 15878 and *A. macra* share many properties. Both are unable to degrade adenine, calcium-malate, chitin, elastin, guanine, keratin, starch, testosterone, tyrosine, and xanthine. Neither produces $H_2S$ or melanoid pigments. Both cultures degrade casein, DNA and gelatin, produce catalase and phosphatase, and synthesize a polyether antibiotic. They have the same tolerance to NaCl; both grow on sodium butyrate; and they have the same cell-wall type. *A. macra* and NRRL 15878 differ in carbon-utilization pattern, esculin and hypoxanthine degradation, resistance to antibiotics, temperature range, urease production, and the reduction of nitrate.

*A. macra* and NRRL 15878 share many cultural characteristics, notably the absence of aerial mycelia. However, there are significant differences. The reverse side of NRRL 15878 is gray to a yellowish brown; *A. macra* on many media produces a red color. This distinction is most clearly seen on glucose-asparagine agar. On this medium *A. macra* produces a pink aerial growth, whereas NRRL 15878 produces none. These cultural comparisons are shown in Table I.

The morphology of NRRL 15878 is similar to that of *A. macra*. Both have poorly developed aerial mycelia that belongs in the Rectus-flexibilis (RF) section of Pridham [T. G. Pridham, C. W. Hesseltine, and R. C. Benedict, "A Guide for the Classification of Streptomycetes According to Selected Groups," *Appl. Microbiol.* 6:52–79 (1957). Spore surface ornamentation is smooth.

The differences and similarities between NRRL 15878 and *A. macra* are summarized in Table IV.

TABLE IV

| Summary Comparison of NRRL 15878 and *A. macra* | |
|---|---|
| Similarities | Differences |
| Morphology | Antibiotic resistance |
| Physiological properties | Carbon-utilization pattern |
| Polyether synthesis | Cultural characteristics |

TABLE IV-continued

| Summary Comparison of NRRL 15878 and *A. macra* | |
|---|---|
| Similarities | Differences |
| Scarcity of aerial hyphae | Degradation of esculin |
| | Degradation of hypoxanthine |
| | Nitrate reduction |
| | Spore shape and size |
| | Temperature range |
| | Urease production |

Table V shows these similarities and differences in greater detail.

TABLE V

| Comparison of NRRL 15878 and *A. macra* | | |
|---|---|---|
| Test | NRRL 15878 | *A. macra* |
| Aerial hyphae formation | rare | rare |
| Carbon-utilization pattern | different (see Table II) | |
| Catalase degradation of: | | |
| adenine | − | − |
| calcium malate | − | − |
| casein | + | + |
| chitin | − | − |
| DNA | + | + |
| elastin | − | − |
| esculin | + | − |
| gelatin | + | + |
| guanine | − | − |
| hypoxanthine | − | + |
| keratin | − | − |
| starch | − | − |
| testosterone | − | − |
| tyrosine | − | − |
| xanthine | − | − |
| Growth in liquid media | colorless | red-orange |
| Growth on Na butyrate | + | + |
| $H_2S$ production | − | − |
| Melanoid pigments | − | − |
| NaCl tolerance | 2 percent | 2 percent |
| Nitrate reduction | − | + |
| Phosphatase | + | + |
| Polyether synthesis | + | + |
| Resistance pattern to antibiotics | different (see Table III) | |
| Resistance to lysozyme | + | ND |
| Reverse side color | gray → brown | brown → orange |
| Soluble pigment | brown | brown |
| Spore chains | RF | RF |
| Spore surface | smooth | smooth |
| Temperature range | 15–42° | 15–37° |
| Urease production | + | − |
| Spore shape | oblong | oval |
| Spore size | 0.5–0.7 × 0.9–1.3 μm | 0.8–1.0 × 1.2–2.0 μm |

These comparisons indicate that the NRRL 15878 culture is significantly different from other species of Actinomadura and represents a new species for which the name *Actinomadura oligospora* sp. nov. is proposed. The specific epithet (O.ligo.spor.a: L. Adj. oligo few, L.n. spora spored, *oligospora* few spored) refers to the relative absence of sporophores in the organism. Strain NRRL 15878 is the type strain of *A. oligospora*.

As is the case with other organisms, the characteristics of the A80190-producing culture of this invention, *Actinomadura oligospora* NRRL 15878, are subject to variation. Recombinants, mutants or variants of the strain may be obtained by methods in the art. For example, mutants can be obtained by treatment with various known physical and chemical mutagens such as ultraviolet light, X rays, gamma rays and chemicals such as N-methyl-N'-nitro-N-nitrosoguanidine. Natural and induced variants, mutants and recombinants of *Actinomadura oligospora* NRRL 15878 which retain the characteristic of A80190 production are part of this invention.

The culture medium used to grow *Actinomadura oligospora* NRRL 15878 can be any one of a number of media. For economy in production, optimal yield, and ease of production isolation, however, certain culture media are preferred. Thus, for example, a preferred carbohydrate source in large-scale fermentation is glucose, although ribose, xylose, fructose, galactose, mannose, mannitol, potato dextrin and the like can also be used. Glycerol and lipids support little or no growth or antibiotic production when used as the primary carbon source. In combination with glucose, they enhance biomass, but depress antibiotic production.

A preferred nitrogen source is collagen hydrolysate, although enzyme-hydrolyzed casein, meat peptones, fish meal, liver meal, and the like are also useful. Among the nutrient inorganic salts which can be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism. Foaming is not usually a problem, but small amounts (i.e. 0.2 ml/L) of an anti-foam agent such as polypropylene glycol may be added to large scale fermentation media if needed.

For production of substantial quantities of antibiotic A80190, submerged aerobic fermentation in tanks is preferred. Small quantities of A80190 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

A80190 is produced by the A80190-producing organism when grown at temperatures between about 25° and about 37° C. An optimum temperature for A80190 production appears to be about 30°–32° C.

As is customary in submerged aerobic culture processes, sterile air is blown into the vessel from the bottom while the medium is stirred with conventional turbine impellors. The maximum oxygen uptake of the fermentation under the conditions used thus far has not exceeded about 0.2 mM/L/minute. For example, in a fully baffled 165-liter fermentor containing approximately 115 liters of broth, an aeration rate of 0.125 v/v/m with an agitation rate of 200 rpm is sufficient to maintain the level of dissolved oxygen at or above 30% of saturation.

Production of antibiotic A80190 can be followed during the fermentation by testing samples of the broth for antibiotic activity against organisms known to be sensitive to the antibiotic. One assay organism useful in testing A80190 is *Bacillus subtilis* ATCC 6633. The bioassay is conveniently performed by the agar-well plate test.

Following its production under submerged aerobic fermentation conditions, A80190 can be recovered from the fermentation medium by methods used in the fermentation art. The antibiotic activity produced during fermentation of the A80190-producing organism occurs both in the filtered broth and in the mycelial mass. Maximum recovery of A80190 is accomplished, therefore, by initially filtering the medium to separate the broth from the mycelial mass. The filtered broth and the mycelial mass can then be purified separately to give their respective portion of A80190. A variety of techniques may be used in this purification. A preferred technique for purification of the filtered broth involves adjusting it to a pH of about 9 and extracting with a suitable solvent such as, for example, ethyl acetate. The extracting solvent can then be evaporated under vacuum to give the broth portion of A80190. A preferred method of purifying the mycelial mass is to extract the separated mycelial filter cake with a suitable solvent such as, for example, methanol or acetone. The extracting solvent is then evaporated under vacuum to give a concentrated aqueous solution. This aqueous solution is then adjusted to a pH of about 9 and is extracted with a suitable solvent such as, for example, ethyl acetate. The extracting solvent is then concentrated under vacuum to give the mycelial portion of A80190. The broth and mycelial portions of the A-80190 complex are further purified by similar procedures. A preferred procedure involves silica gel chromatography.

Alternatively, the culture solids, including medium constituents and mycelium can be used without extraction or separation, but preferably after removal of water, as a source of A80190. For example, after production of A80190, the whole fermentation broth can be dried by lyophilization, by drum-drying, or by azeotropic distillation and drying. The dried broth is then mixed directly into feed premix.

In order to illustrate more fully the operation of this invention, the following examples are provided:

EXAMPLE 1

Preparation of A80190

A. Shake-flask Fermentation of A80190

The culture *Actinomadura oligospora* NRRL 15878, either as a lyophilized pellet or as a suspension maintained in liquid nitrogen, is used to inoculate a seed medium having the following composition:

| SEED MEDIUM | |
| --- | --- |
| Ingredient | Amount (%) |
| Glucose | 1.0 |
| Soluble starch | 2.0 |
| Yeast extract | 0.5 |
| Enzymatic hydrolysate of casein* | 0.5 |
| CaCO$_3$ | 0.1 |
| Deionized water | q.s. 1 liter |

NaOH was added to raise the pH of the medium to about 7.2 before sterilizing.
*NZ Amine A, Sheffield Chemical Co., Norwich, N.Y.

Slants or plates are prepared by adding 2.5% agar to the seed medium. The inoculated slant is incubated at 30° C. for from about 10 to about 14 days. The mature slant culture is scraped with a sterile tool to loosen the spores and remove and mascerate the mycelial mat. About one-fourth of the loosened spores and culture growth thus obtained is used to inoculate 50 ml of a first-stage seed medium.

The inoculated first-stage medium is incubated in a 250-ml Erlenmeyer flask at 30° C. for about 48 hours on a shaker orbiting in a two-inch (5.08 cm) circle at 250 rpm.

This incubated first-stage medium (0.4 ml) is used to inoculate 50 ml of a production medium having the following composition:

| Ingredient | Amount (%) |
| --- | --- |
| Glucose | 3.0 |
| N—Z Amine A | 0.4 |
| Collagen hydrolysate* | 0.5 |
| $MgSO_4.7H_2O$ | 0.05 |
| $CaCO_3$ | 0.2 |
| Cold tap water | q.s. 1 liter |

(Presterilization pH adjusted to 7.0)
*IPC 3, -Inland Industrial Molasses Co., Dubuque, Iowa The inoculated production medium is incubated in a 250-ml wide-mouth Erlenmeyer flask at 30°-32° C. for 8 to 10 days on a shaker orbiting in a two-inch circle at 250 rpm.

B. Tank Fermentation of A80190

In order to provide a larger volume of inoculum, 10 ml of incubated first-state medium, prepared as described in Section A, is used to inoculate 400 ml of a second-stage growth medium having the same composition as that of the first-stage medium. This second-stage vegetative medium is incubated in a twoliter widemouth Erlenmeyer flask for about 48 hours at 30° C. on a shaker orbiting in a two-inch circle at 250 rpm.

Incubated second-stage vegetative medium (800 ml) thus prepared is used to inoculate 100 liters of sterile production medium, prepared as described in Section A. The inoculated production medium is allowed to ferment in a 165-liter stirred fermentation tank for 8 to 10 days at a temperature of 30°-32° C. Low airflow (0.12-0.25 v/v/m) and low rpm (150-200) in the stirred vessel maintain a dissolved oxygen level above 30% of air saturation.

EXAMPLE 2

Isolation of A80190

Whole fermentation broths from two 100-L tanks were combined (207 L) and filtered through a filter press with the aid of Hyflo Supercel. The mycelial filter cake was extracted by circulating methanol (40 L) through the filter press. Acetone can also be used as an extractant. The methanol extract, concentrated in vacuo to a volume of about 15 L, was combined with the broth filtrate (182 L). This was adjusted to pH 9 with 1 N sodium hydroxide, and the resulting solution was extracted with an equal volume of ethyl acetate. The ethyl acetate extract was concentrated to a volume of about 700 ml. Water (1 L) was added to the concentrated extract; the pH was adjusted to 9.0 with sodium hydroxide; and the mixture was extracted twice with toluene (1 L), maintaining the pH at 9.0. The toluene extracts were combined and concentrated in vacuo to give an oily residue containing A80190.

The residue was dissolved in toluene (100 ml) and applied to a column containing 2 L of silica gel (Woelm, 70–150 mesh) in toluene. The column was eluted first with toluene (10 L) and then with toluene:ethanol mixtures (49:1, 10 L) and (48:2, 10 L), collecting 1-L fractions. Elution was monitored by bioassay and TLC. Fractions containing A80190 were combined and concentrated. The residue was dissolved in dioxane and freeze-dried to yield 13.6 g of crude A80190.

EXAMPLE 3

Purification of A80190

Crude A80190 (20.4 g), obtained from four 100-L tanks as described in Examples 1 and 2, was dissolved in acetonitrile (200 ml). The solution was applied to a column containing 2 L of silica gel (Woelm, 70–150 mesh) in acetonitrile. The column was washed with acetonitrile (10 L) and eluted sequentially with acetonitrile:acetone mixtures (95:5, 2 L), (9:1, 10 L), (4:1, 10 L) and (7:3, 10 L), collecting 1-L fractions.

Elution was monitored by bioassay, using *Bacillus subtilis*. Fractions containing A80190 were combined and concentrated. The residue was dissolved in dioxane and freeze-dried to yield 15.8 g of purified A80190.

EXAMPLE 4

Crystallization of A80190

Purified A80190 (28.2 g), was dissolved in acetone (500 ml). Water (500 ml) was added, and the pH was adjusted to 5.0 with dilute hydrochloric acid. The resulting solution was allowed to stand at room temperature for 20 hours for crystallization to occur. The crystals were separated by filtration, washed with water and dried in a vacuum oven to yield 25.9 g of crystalline A80190 (acid form).

EXAMPLE 5

Chromatographic Identification of A80190

I. TLC on silica gel
System: acetonitrile:acetone (1:1)
$R_f = 0.59$
Detection:
  *Bacillus subtilis*
  Vanillin-$H_2SO_4$ spray
II. HPLC
Adsorbent: μBondapak C18 (4×300-mm column)
Solvent system: acetonitrile:tetrahydrofuran:$H_2O$ (6:1:3) containing 1 percent $H_3PO_4$; adjusted to pH 3.0 with $NH_4OH$
Detection: refractometer
Flow rate: 3.0 ml/min
Retention time: 9.7 min

I claim:

1. In the process for producing antibiotic A80190, the improvement which comprises cultivating *Actinomadura oligospora* NRRL 15878, or an A80190-producing mutant thereof, in a culture medium containing assimilable sources of carbon, nitrogen, and inorganic salts under submerged aerobic fermentation conditions until a recoverable amount of antibiotic A80190 is produced.

2. The process of claim 1 which includes the additional step of separating A80190 from the culture medium.

3. The process of claim 1 wherein *A. oligospora* NRRL 15878 is used.

4. A biologically purified culture of the microorganism *Actinomadura oligospora* NRRL 15878, or an A80190-producing mutant or recombinant thereof.

5. The culture of claim 4 which is *A. oligospora* NRRL 15878.

* * * * *